United States Patent [19]

Miyataka et al.

[11] Patent Number: 5,322,066
[45] Date of Patent: Jun. 21, 1994

[54] DISCRETELY MODIFIABLE IMAGING IN ULTRASONIC DIAGNOSTIC EQUIPMENT

[75] Inventors: Mutsumi Miyataka; Masaki Iwasaki, both of Kyoto, Japan

[73] Assignee: Shimadzu Corporation, Kyoto, Japan

[21] Appl. No.: 61,255

[22] Filed: May 17, 1993

[30] Foreign Application Priority Data

May 22, 1992 [JP] Japan .................. 4-130500

[51] Int. Cl.5 .............................. A61B 8/00
[52] U.S. Cl. ................ 128/660.04; 128/660.01
[58] Field of Search .............. 128/660.01, 660.04, 128/660.05, 661.09, 660.10

[56] References Cited

U.S. PATENT DOCUMENTS

| | | | |
|---|---|---|---|
| 4,612,937 | 9/1986 | Miller | 128/660.05 |
| 4,917,096 | 4/1990 | Englehart et al. | 128/660.10 |
| 5,215,093 | 6/1993 | Miyazaki et al. | 128/661.09 |

Primary Examiner—William E. Kamm
Assistant Examiner—George Manuel
Attorney, Agent, or Firm—Nikaido, Marmelstein, Murray & Oram

[57] ABSTRACT

In ultrasonic diagnostic equipment processing signals echo-reflected from ultrasonic pulses beamed into a patient and providing composite display of patient-related diagnostic information including organic information, the comprehensive diagnostic information is discretely stored as various imaging data into separate display memories, and is furthermore externally storable through VTR recording such that the information can be retrieved for regeneration. A selector selects between either real-time imaging derived from the display memories, or regeneration imaging obtained from a pseudo-video combined signal stored in the VTR, for input to a color palette as an imaging processor which color encodes and combines data for composite imaging. Separate imaging modification processes are post real-time executable upon the discretely regenerated imaging data retrieved from the VTR for altered display on a monitor of the equipment.

20 Claims, 7 Drawing Sheets

DISCRETELY MODIFIABLE IMAGING IN ULTRASONIC DIAGNOSTIC EQUIPMENT

BACKGROUND OF THE INVENTION

The present invention relates to ultrasonic diagnostic equipment; particularly it relates to diagnostic equipment which employs ultrasonic probing to examine a patient, and generates composite display of patient-related diagnostic information including organic information derived from the ultrasonic probe.

Ultrasonic diagnostic equipment as used in the medical field provides tomographic display of real-time cardiac data, and also displays such information on patient bloodstream as flow velocity distribution, calculated from a volume sampled by the pulsed Doppler method. Furthermore, it is well known to provide tomographic and bloodstream flow-velocity displays arranged on a single monitor of the ultrasonic diagnostic equipment.

One method of composition-imaging cardiac information provides dual display of two-dimensional tomographic organic information together with real-time bloodstream information such as average flow velocity and flow velocity distribution. In this method, the tomographic organic information and bloodstream information are digitalized and combined, and further converted by a color palette into R (red), G (green) and B (blue) color display signals. The R, G, and B color signals are output to a display monitor, wherein the detected bloodstream information is displayed in full color, superimposed on the ordinary tomographic image display.

A video tape recorder (VTR) or a magnetic-optical disc (MO) can be used as external storages to record the composite imaging. In the former instance a composite television signal generated from imaging data is recorded by the VTR, and in the latter, the composite imaging color display signals are recorded onto the MO.

The imaging data recorded on the VTR are regenerated by retrieving the television composite signal and demodulating therefrom R, G and B color signals which are output to the display monitor. Wherein the MO is the external storage, the R, G and B color signals are retrieved, converted into analog signals and output to the monitor.

According to the aforedescribed organic data storage and retrieval system, in recording into external storage the composite full-color imaging of the tomographically displayed organic information and of the real-time bloodstream information it is impossible to separate, for example, bloodstream average flow velocity data or tomographic imaging organic data from the retrieved or regenerated signals. Moreover, it is thus impossible to perform such post data-retrieval processes requiring discrete data as altering luminance or chrominance of the color display signals, or altering the imaging gamma; nor is it possible to change other of the retrieved imaging data, or measured outcome.

SUMMARY OF THE INVENTION

It is an object of the present invention to enable post-retrieval processing of regenerated imaging data from external storage in ultrasonic diagnostic equipment.

Ultrasonic diagnostic equipment according to an aspect of the present invention beams ultrasonic waves into an patient under examination and provides composite display of diagnostic information including organic information. With the inventive equipment, various organic information obtained from reflected ultrasonic echo signals is stored into a corresponding plurality of memories. The plural diagnostic information is discretely storable into a VTR. A selector selects retrieval of either the plural information as discretely stored in the VTR or the plural information stored in the memories, and the selected information is composite-imaging data converted for display. It is therein possible to discretely execute modifying processes upon the imaging data post-retrieval from external storage.

The foregoing and other objects and advantages of the present invention will be more fully apparent from the following detailed description made with reference to the accompanying drawings.

DESCRIPTION OF PREFERRED EMBODIMENTS

First Embodiment

Figure 1:
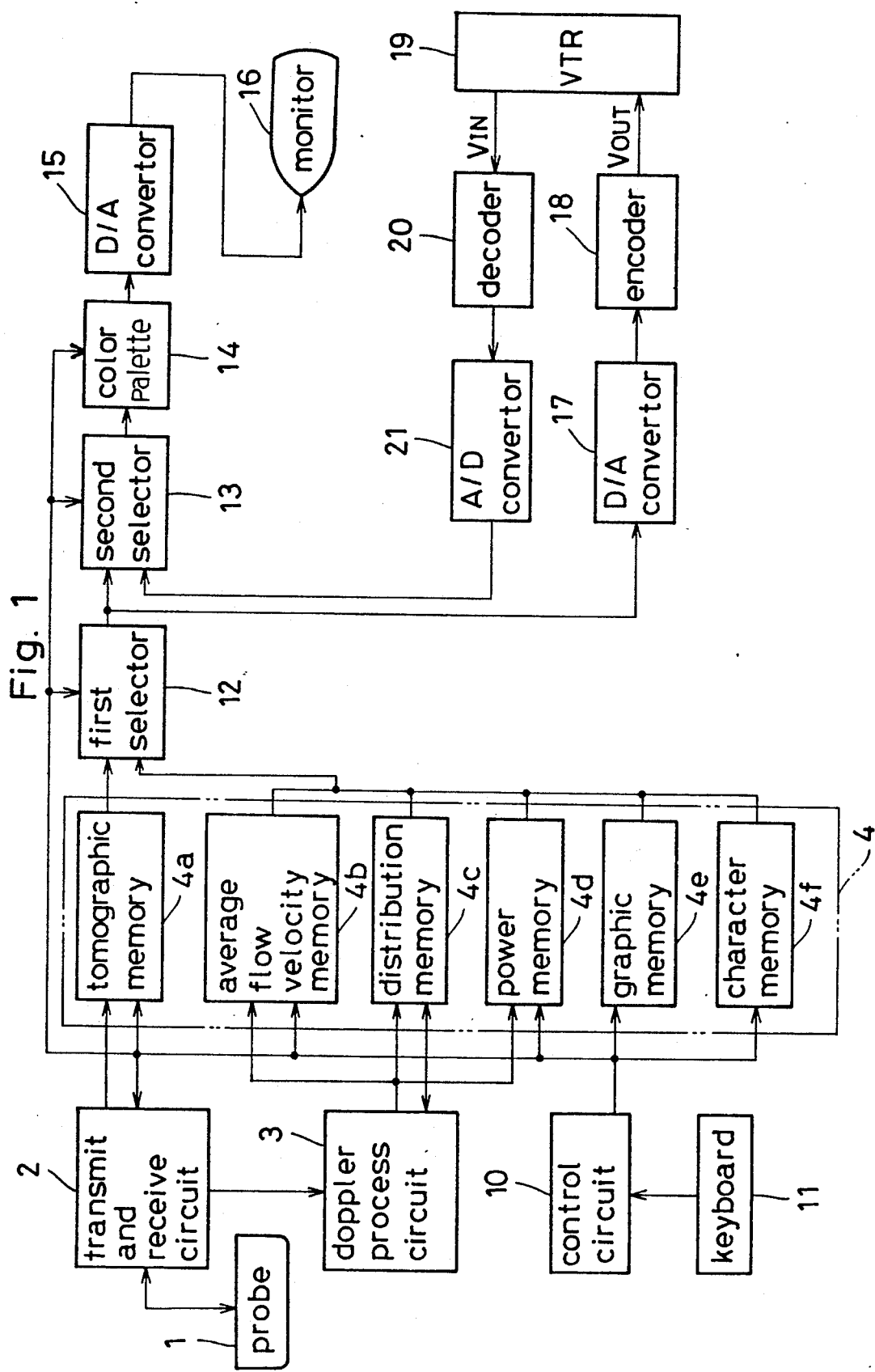
FIG. 1 is a highly schematic block diagram of ultrasonic diagnostic equipment according to the first embodiment of the present invention.

Ultrasonic diagnostic equipment according to the first embodiment of the present invention as schematically represented by FIG. 1 provides composite display of tomographic imaging and bloodstream information in color Doppler mode, as well as display of tomographic imaging and bloodstream information arranged on a single monitor in a B/D mode.

The probe 1 beams ultrasonic waves into an organism under examination and receives reflected signals from which organic information is obtained. The probe 1 contains an array of transducers and is connected to a transmit and receive circuit 2.

The transmit and receive circuit 2 consists inter alia of a high-frequency oscillator which excites the transducer array to emit ultrasonic waves; a receiver which receives signals detected from echoed ultrasonic waves; a delay circuit and a delay amount selection circuit for electronic scanning of the ultrasound beam; and a waveform shaper and a detection circuit which derive tomographic imaging data from the organic scanning. The transmit and receive circuit 2 is connected to a Doppler process circuit 3, which calculates blood stream information including average flow velocity, velocity distribution and flow power, based upon the reflected signals received by the transmit and receive circuit 2.

Connected to the transmit and receive circuit 2 and the Doppler process circuit 3 is a display storage 4. The display storage 4 comprises tomographic memory 4a, average flow velocity memory 4b, velocity distribution memory 4c, flow power memory 4d, graphic memory 4e and character memory 4f. The tomographic memory 4a stores tomographic imaging data for one display raster obtained by the transmit and receive circuit 2. The memories 4b, 4c and 4d respectively store the average flow velocity, velocity distribution and flow power data from the Doppler process circuit 3 for the display raster. The graphic memory 4e stores graphic data used for displaying markers, scales, and trace lines in a measurement mode, and an ultrasound beam line of sight angle correction marker in the Doppler mode. The character memory 4f stores alphanumeric data used for displaying date, time, and patient identification, as well as measurement outcome.

Connected to each memory 4a–4f of the display storage 4 is a first selector 12, which outputs data from the tomographic memory 4a, from the graphic memory 4e and the character memory 4f, and from two stores selected from among the average flow velocity memory 4b, the velocity distribution memory 4c and the flow power memory 4d according to given display modes. For example, in the color Doppler mode, the first selector 12 outputs data stored in the tomographic memory 4a, the average flow velocity memory 4b, the velocity distribution memory 4c, the graphic memory 4e and the character memory 4f. Input terminals of a second selector 13 are connected to the first selector 12 and an A/D convertor 21, wherein the second selector 13 selects between outputs of either the first selector 12 or the A/D convertor 21. That is, either real-time data or regenerated data is selected.

Figure 2:
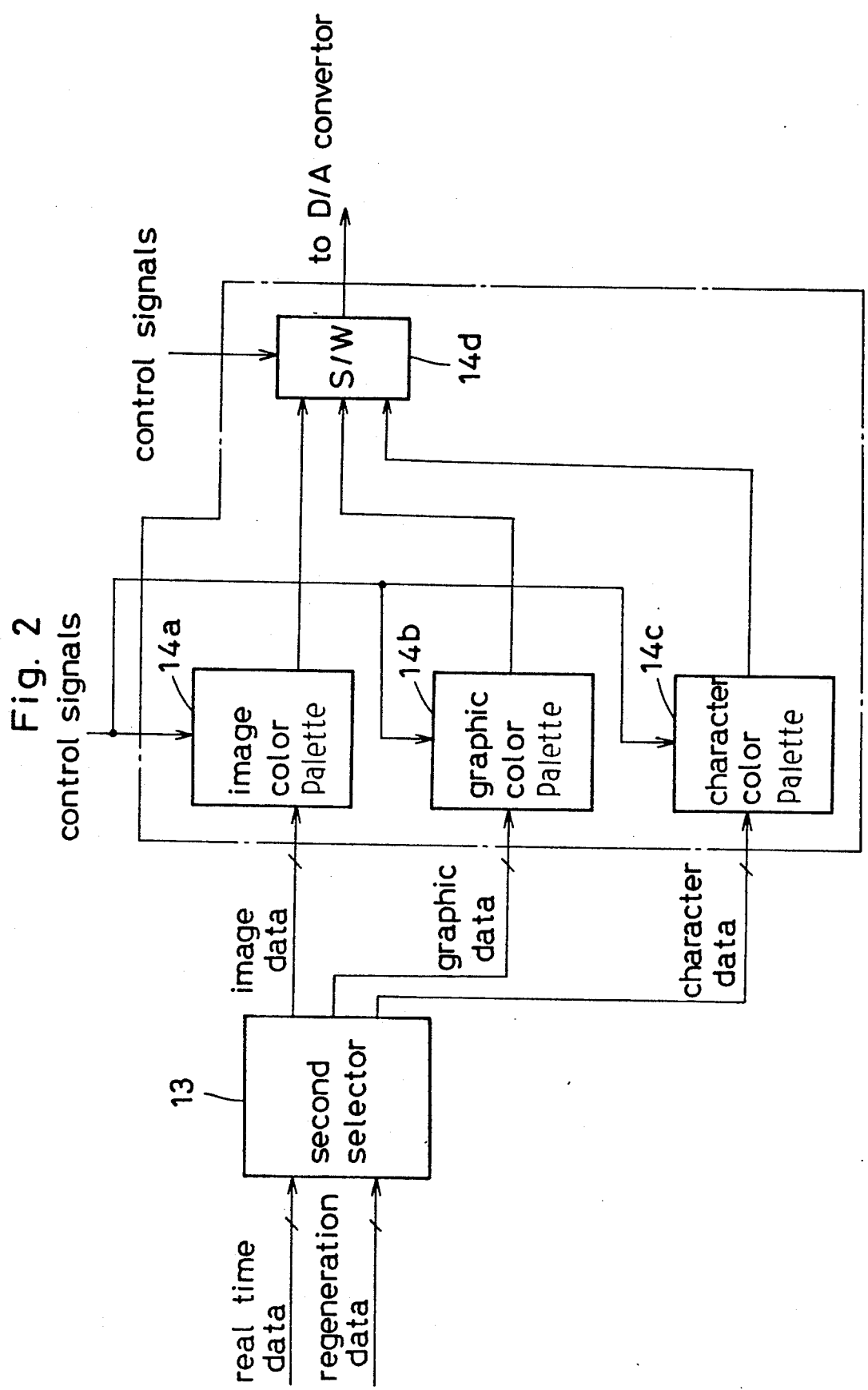
FIG. 2 is a schematic block diagram of a color palette.

A color palette 14 is connected to the second selector 13. The color palette 14 color encodes the discrete input data and converts them into corresponding R, G, and B color signals. The color palette 14 comprises, as shown in FIG. 2, an image color palette 14a for color encoding imaging data consisting of the tomographic imaging data and the Doppler data from the two selected discrete bloodstream data, a graphic color palette 14b for color encoding graphic data, a character color palette 14c for color encoding alphanumeric data, and a switch 14d for selecting data output from the color palettes 14a–14c. With regard to the data selected by the second selector 13, the aforedescribed imaging data, and the graphic data and the character data are respectively input to the image color palette 14a, the graphic color palette 14b and the character color palette 14c.

Figure 3:
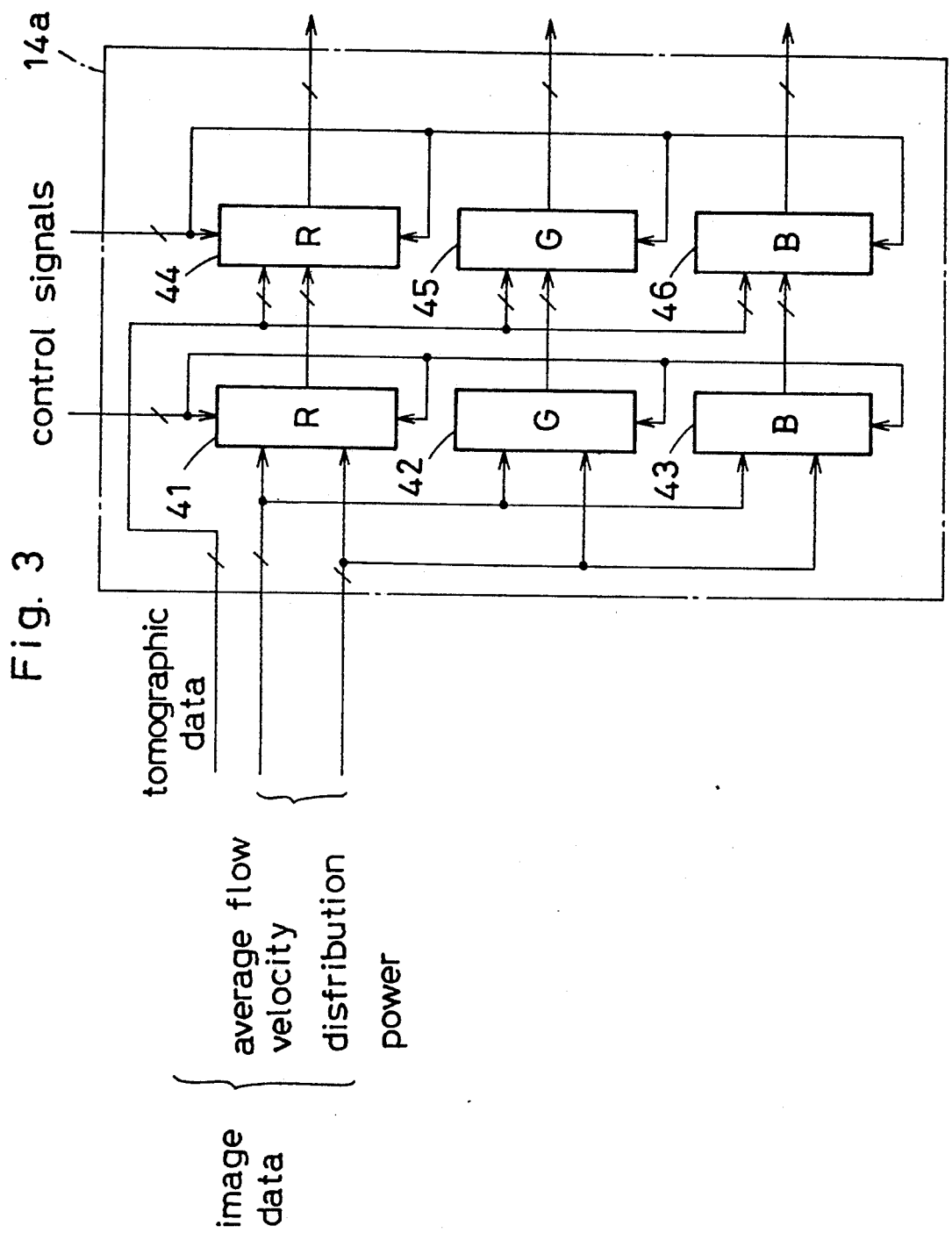
FIG. 3 is a schematic block diagram of an imaging data color encoder of the color palette.

The image color palette 14a comprises, as shown in FIG. 3, RAMs 41–46 for generating encoded R, G and B color signals. First-stage RAMs 41–43 store two discrete bloodstream data selected from among the average flow velocity, velocity distribution and flow power data in the first selector 12 according to the display mode. Second-stage RAMs 44–46 store the tomographic imaging data and outputs from the first-stage RAMs 41–43.

Figure 4:
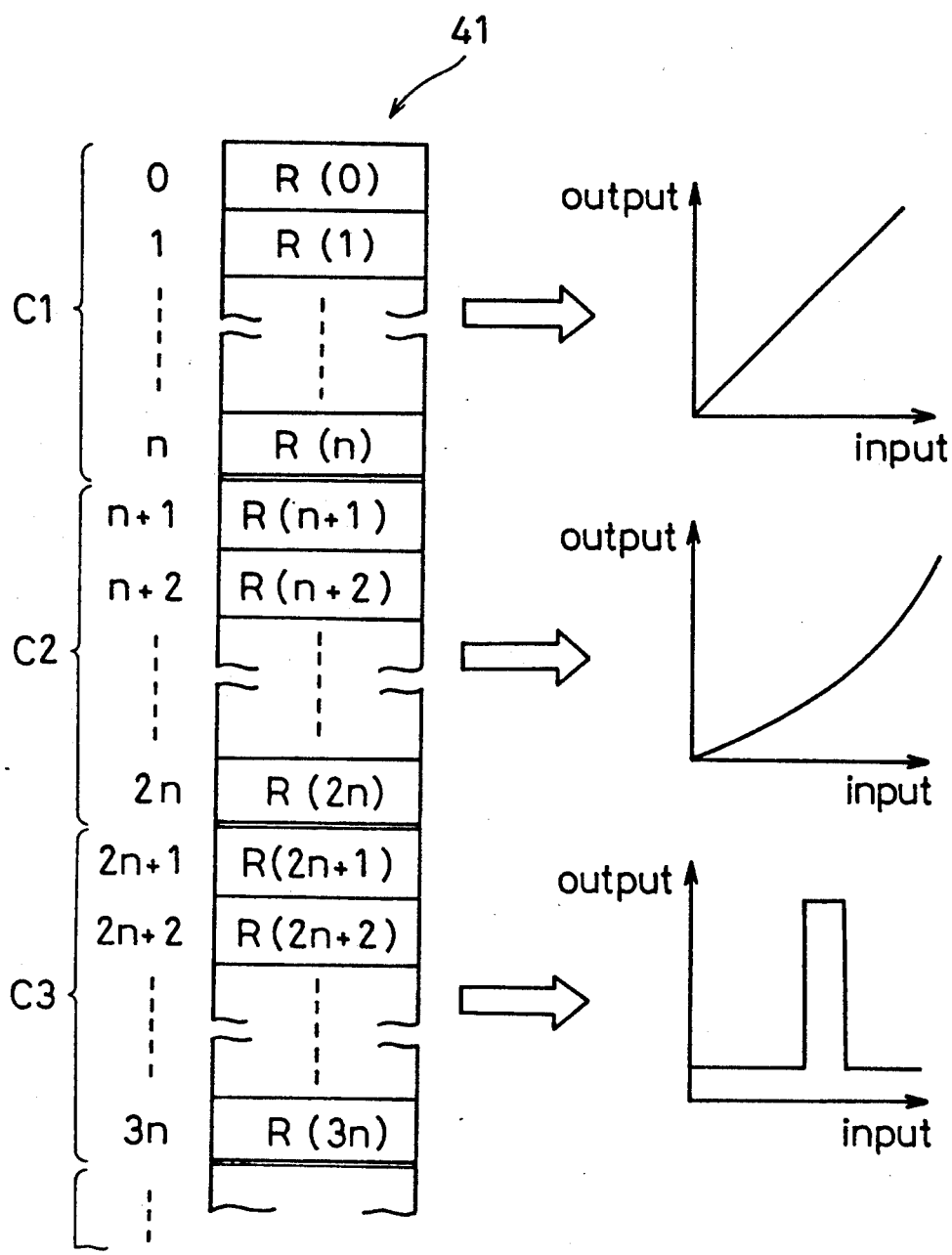
FIG. 4 represents addressing of RAM data tables of the imaging data color encoder.

Each RAM functions as a data table to which addresses determined by the two discrete bloodstream data are input, and from which data converted according to certain gamma of imaging characteristics are output. For example, RAM 41 stores data R (0) through R (n) for straight-$\gamma$ data conversion, as shown in FIG. 4. Data R (n+1) through R (2n) for parabolic-$\gamma$ data conversion are stored in addresses (n+1) through (2n); and data R (2n+1) through R (3n) for highlighting-$\gamma$ data conversion are stored in addresses (2n+1) through (3n). Data for other gamma data conversion are stored following address (3n+1). Control signals C1, C2, C3 . . . from a control circuit 10 determine the gamma of data conversion. Particularly, the upper several bits of the addresses input to the RAM 41 comprise the control signals, wherein lower several bits thereof comprise the two discrete bloodstream data input from the second selector 13.

Connected to the color palette 14 is a D/A converter 15, which converts the R, G and B digital color signals into analog signals and outputs them to the monitor 16. The monitor 16 displays composite imaging. The switch 14d of the color palette 14 may be provided at an output of the D/A convertor.

The output terminal of the first selector 12 is also connected to a D/A convertor 17. The D/A convertor 17 converts the discrete data stored in the display storage 4 into analog signals and sends them to an encoder 18. Such an encoder is ordinarily used for generating a television composite signal from R, G and B color signals, but in this case it generates a "pseudo-video" combined signal using the discrete data in the display storage 4 instead of the R, G and B color signals. The encoder 18 generates a pseudo-video combined signal in the color Doppler mode using the average flow velocity data stored in the average flow velocity memory 4b as the R signal, distribution data stored in the distribution memory 4c as a G signal, and tomographic imaging data stored in the tomographic memory 4b as a B signal. The graphic data and character data are encoded by the encoder 18 and written in between retrace lines of the pseudo-video combined signal. A visual tape recorder (VTR) 19 is connected to the encoder 18, wherein it records the pseudo-video combined signal generated by the encoder 18.

Output terminals of the VTR 19 are connected to a decoder 20 to which the pseudo-video combined signal recorded by the VTR 19 is fed in signal regeneration. The decoder 20 separates the pseudo-video combined signal into the discrete tomographic imaging data, and the Doppler data, etc. In the exemplary color Doppler mode, the bloodstream average flow velocity, and velocity distribution data, and the tomographic imaging data are separated from the pseudo-video combined signal. Graphic and character data being also encoded into the pseudo-video combined signal are decoded by the decoder 20, which contains discrete stores corresponding to the average flow velocity, velocity distribution and flow power memories 4b, 4c, and 4d. The discrete data are sent to an A/D convertor 21 wherein they are digitized and then sent to the input terminal of the second selector 13 as explained before.

The control circuit 10 outputs control signals to the transmit and receive circuit 2, the Doppler process circuit 3, the display storage 4, the first selector 12, the second selector 13 and the color palette 14. The control circuit 10 outputs selection signals to the first selector 12 and the second selector 13, and outputs data for conversion color encoding as well as various correction data to the color palette 14. The control circuit 10 further controls write-in and read-out timing of the display storage 4. The control circuit 10 also outputs to the graphic memory 4e and the character memory 4f stored data according to the display mode.

A keyboard 11 is connected to the control circuit 10 for commanding the display mode selection, and for changing the various parameters in operation of the color palette 14.

In working operation, then, of the ultrasonic diagnostic equipment constructed as aforedescribed, the transmit and receive circuit 2 provides high-frequency pulses to the probe 1, actuating the probe 1 to beam ultrasonic waves into the patient under examination, and it detects ultrasonic signals reflected at organic interfaces within the patient's body. The reflected ultrasonic echo signals are input to the transmit and receive circuit 2, wherein the signals are processed to produce inter alia tomographic imaging data, which is then stored into the tomographic memory 4a. The reflected echo signals are also fed to the Doppler process circuit 3, wherein the signals are cross-detected, and the bloodstream average flow velocity data, the velocity distribution data and the flow power data are calculated by auto-correlation calculation.

Meanwhile, the graphic memory 4e stores data for such graphic display as a marker indicating Doppler line of sight for angle correction, and it stores output from the control circuit 10, as well as various display scales. The display mode input through the keyboard 11 determines which graphic data is to be output from the control circuit 10. The character memory 4f stores date/time and patient ID data output from the control circuit 10 according to input of the keyboard 11, or the measured outcome calculated by the control circuit 10. Data stored in each memory 4a–4f of the display storage 4 are read out according to the first selector 12 selection. In the present case, the tomographic memory 4a, the graphic memory 4e, the character memory 4f, and the two bloodstream data memories from the among memories 4b, 4c, 4d are selected and their data are read out to the second selector 13 and the D/A convertor 17.

Wherein recording of imaging data is commanded through the keyboard 11, the data are combined into the pseudo-video combined signal by the encoder 18 and recorded into the VTR 19. Therein, the encoder 18 analyzes the tomographic imaging data and the two selected discrete bloodstream data as analogous to R, G, and B signals respectively, thereby generating the pseudo-video combined signal. The character and graphic data are encoded and written in between the retrace lines of the pseudo-video combined signal, which is then recorded by the VTR 19.

The second selector 13 selects between either the real-time data of the first selector 12 or the data regenerated through the A/D convertor 21, according to control signals received from the control circuit 10. The selected data are sent to the color palette 14, wherein they are color encoded, which converts them into R, G and B color signals, and combined.

In the color Doppler mode, the tomographic imaging data, the average flow velocity data, the velocity distribution data, the graphic data and the character data are selected by the first selector 12 and are sent to the color palette 14 through the second selector 13. In the color palette 14, the tomographic imaging data, the average flow velocity data and the velocity distribution data are stored into the image color palette 14a, the graphic data is stored into the graphic color palette 14b, and the character data is stored into the character color palette 14c. The data (R, G, B signals) as color encoded by each color palette 14a–14c are switched by the switch 14d at intervals corresponding to each pixel change, and sent to the D/A convertor 15. The switch 14d is controlled by the control signals from the control circuit 10. The priority level of each pixel data is as follows:

character data > graphic data > image data

The imaging signals converted into analog signals by the D/A convertor 15 generate the television composite signal in the monitor 16 for display thereby.

Figure 5:
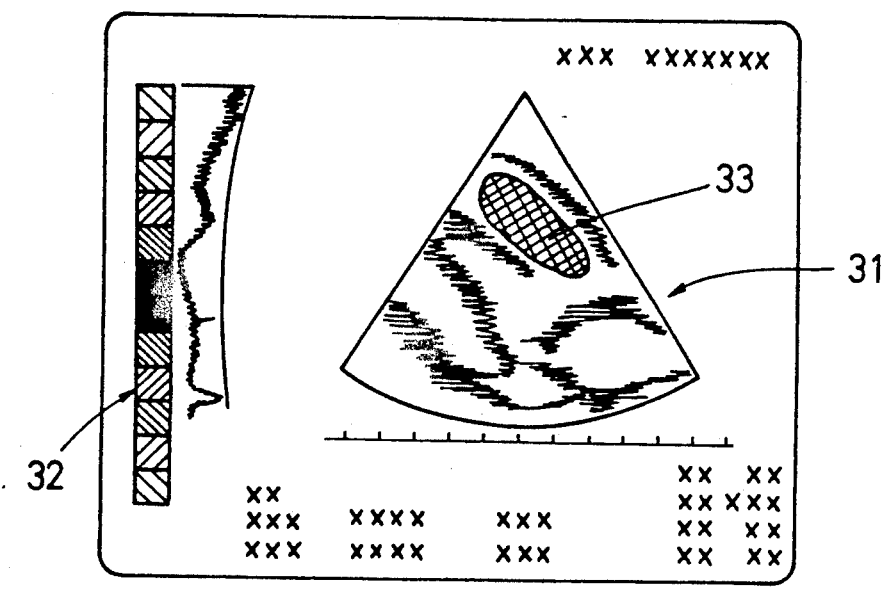
FIG. 5 is schematically depicts an example of a monitor display.

The monitor 16 displays a tomographic B-mode image 31 and a color scale 32 arranged on a single composite display in the color Doppler mode, as shown in FIG. 5. Therein, the heart is displayed in tomographic B-mode imaging, composite-displayed with the bloodstream flow resulting from contraction of the left ventricle (in actuality appearing in blue, indicated in the figure by the double-hatched area 33). That is, the bloodstream average flow velocity data is composite-displayed in real time with contrasting color.

Functions of the image color encoder 14a will be detailed referring to FIGS. 3 and 4.

The imaging data are sent from the second selector 13 to the image color palette 14a. The tomographic imaging data is written into the second-stage RAMs 44–46 for generation of the R, G and B television color signals. The two selected discrete bloodstream data are written into the first-stage RAMs 41–43 for generation of R, G and B color signals. Each of the RAMs 41–46 also receives control signals from the control circuit 10.

For example, the two selected discrete bloodstream data written into the first-stage RAM 41 for the R signal constitute the lower several bits of the address therein. The control signals written into the RAM 41 by the control circuit 10 constitute the upper several bits of the address. The data in the address constituted by these signals is output to the second-stage RAM 44 for R-signal data output. With reference to FIG. 4, if the control signal is C2 and the address indicated is (n+2), the data R (n+2) determining parabolic-gamma of the imaging characteristics is output.

In the second-stage RAM 44 for R signals, the RAM 44 receives as input the data R (n+2) output from the RAM 41, together with the tomographic imaging data and the control signals from the control circuit 10, and outputs the data determining imaging characteristics of a given gamma, similarly to the RAM 41.

The remaining RAMs output G and B data likewise determined by similar operations.

If it is desired to post real-time process the displayed image, the data recorded in the VTR 19 are read out discretely, whereupon the control signals input into the RAMs 41–46 of the color palettes will be changed. If the control signals are changed from C2 to C1, for example, the data R, G, and B (1) are output from the RAMs 41–46. Likewise, the control signals C3 output the data R, G, and B (2n+2).

As explained in the foregoing, in this embodiment the data discretely stored into each memory 4a–4c can be recorded into external storage such that the discrete data can be regenerated upon retrieval. These data can be modified and recombined in post real-time processing for altered display. For example, the color of the display portion 33 indicating bloodstream flow from the left ventricle can be changed, or the tomographic imaging data can be excised.

The scale and marker information shown in FIG. 5 are displayed according to the data stored in the graphic memory 4e. The alphanumeric display such as patient ID is indicated by x's in the figure.

Second Embodiment

The recording medium is not limited to an analog recorder such as the VTR 19. Digital data may be recorded by a magnetic-optical disc device or hard disc device without D/A conversion.

Figure 6:
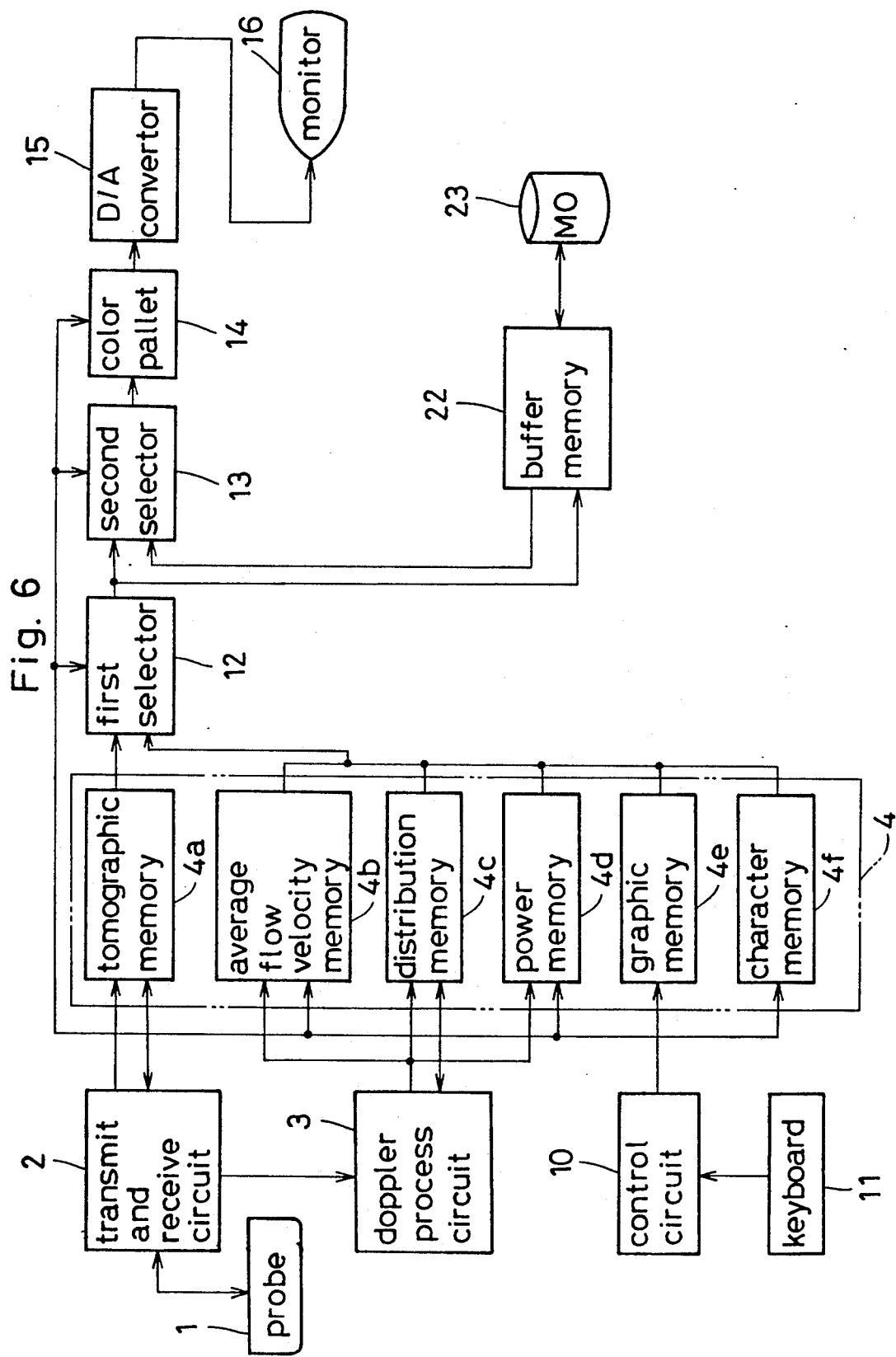
FIG. 6 is a highly schematic block diagram corresponding to FIG. 1 of the second embodiment.

In FIG. 6 illustrating the second embodiment, the structures from the probe 1 to the monitor 16 are in common with the first embodiment; thus their explanation is omitted.

The first selector 12 outputs imaging data to a buffer memory 22 as well as to the second selector 13. The buffer memory 22 is for temporarily storing the data when recording it into the MO 23 or when retrieving the data from the MO 23. The buffer memory 22 outputs the data to the input terminal of the second selector 13. The second selector 13 selects between either the real-time image or the regeneration image retrieved from the MO 23.

In this embodiment, likewise as in the first embodiment, the data discretely stored into the memories 4a–4d are recorded as different files in the MO 23. Each of data read out therefrom to the buffer memory 22 and sent to the color palette 14 through the second selector 13 enables post real-time image processing.

Figure 7:
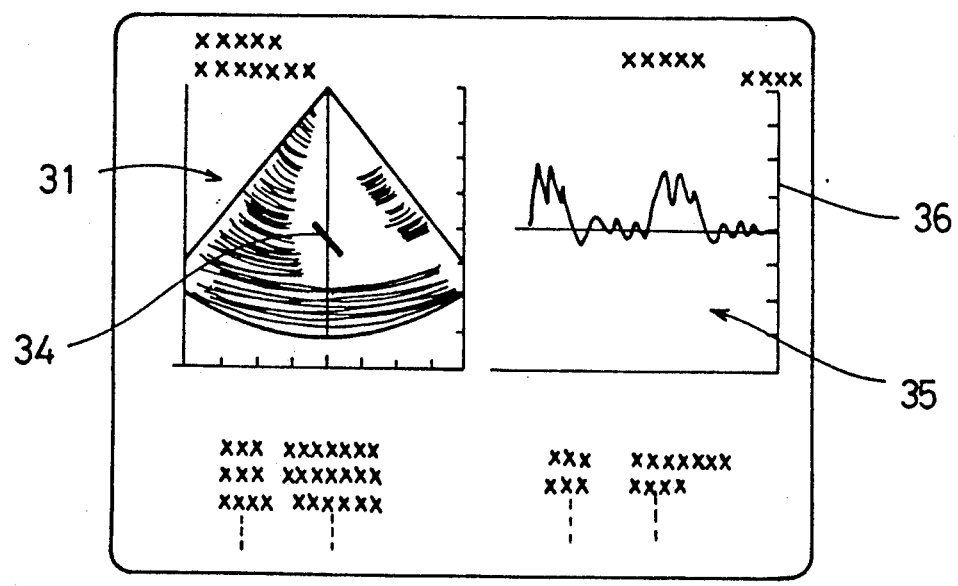
FIG. 7 schematically depicts an example of a monitor display of the second embodiment, corresponding to FIG. 5.

FIG. 7 shows an example of B/D mode imaging display. If a Doppler angle correction mark 34 shown on B-mode tomographic image 31, that is, the angle of the mark for indicating the orientation of the displayed bloodstream is to be changed by commands through the keyboard 11, the image displayed is recorded once into the MO 23. Then, the orientation of the Doppler angle correction mark for the regeneration image is changed through the keyboard 11, command data therefrom being given to the graphic memory 4e as control signals from the control circuit 10, whereby the display image is changed. Also, according to this re-oriented angle, the control circuit 10 outputs to the graphic memory 4e data generating velocity scale 36, displayed to the right of the Doppler image 35, thereby rewriting the data into the graphic memory 4e. In this way, the corrected image can be displayed again according to measurement outcome of the images recorded by the MO 23. Moreover, the corrected image can be recorded into the MO 23.

Other Embodiments (a) The character memory 4d may store data in ASCII format instead of storing the display format as graphic data.

(b) The aforementioned embodiments disclose a VTR and an MO as external storages. The present invention, however, is not limited to them and a hard disc device or a digital video tape recorder may be used for likewise recording data.

Various details of the invention may be changed without departing from its spirit nor its scope. Furthermore, the foregoing description of the embodiments according to the present invention is provided for the purpose of illustration only, and not for the purpose of limiting the invention as defined by the appended claims and their equivalents.

What is claimed is:

1. An ultrasonic diagnostic system for emitting ultrasonic signals into an organism under examination and, through processing echoed ultrasonic signals echoed from the organism, provides composite display of organism-related diagnostic information including organic information, said system comprising:

a probe which beams said ultrasonic signals into a portion of the organism and receives the echoed ultrasonic signals echoed therefrom;

transmit and receive means, for transmitting the ultrasonic signals to said probe, and for processing the echoed ultrasonic signals received by said probe;

memory means for discretely storing diagnostic information obtained from the echoed signals;

recording means for recording into an external storage said diagnostic information as discretely stored in said memory means, to enable correspondingly discrete regeneration of said diagnostic information;

selection means for selecting one of regeneration signal data from said external storage and data from said memory means, as diagnostic information output;

image processing means for forming display data from the diagnostic information output in response to the selection made by said selection means; and display means for displaying the data formed by said image processing means.

2. An ultrasonic diagnostic system according to claim 1, wherein said transmit and receive means comprises a tomographic data processing circuit for obtaining tomographic display data from the echoed ultrasonic signals echoed from the organism, and a Doppler processing circuit for calculating data pertaining to organism bloodstream flow based upon the echoed ultrasonic signals.

3. An ultrasonic diagnostic system according to claim 2, wherein said memory means comprises means for storing the tomographic display data obtained by said tomographic data processing circuit, and means for storing the bloodstream data calculated by said Doppler processing circuit.

4. An ultrasonic diagnostic system according to claim 3, wherein the bloodstream data storing means comprises bloodstream flow data storage for storing data pertaining to bloodstream flow average velocity, flow velocity distribution, and velocity-relative flow power, as calculated by said Doppler processing circuit.

5. An ultrasonic diagnostic system according to claim 4, further comprising bloodstream data selection means for reading out said tomographic display data from said tomographic display data storing means, and for selectively reading out data from said bloodstream flow data storages of said bloodstream data storing means, so as to output to said selection means said tomographic display data together with data from a two of the bloodstream flow data storages.

6. An ultrasonic diagnostic system according to claim 5, wherein said bloodstream data selection means selects data from the two bloodstream flow data storage based upon a display mode selection of said display means.

7. An ultrasonic diagnostic system according to claim 6, wherein said image processing means comprises display data composition means for composing display data based upon the diagnostic information output from said selection means.

8. An ultrasonic diagnostic system according to claim 6, wherein said image processing means further comprises imaging data combining and color-signal encoding means for combining and encoding imaging data based upon the diagnostic information output form said selection means.

9. An ultrasonic diagnostic system according to claim 8, further comprising a control circuit which outputs control signals for controlling the combining and color-signal encoding means to color-encode combined imaging data; wherein said combining and color-signal encoding means contains a plurality of memories each of which functions as a data table which, upon receiving said tomographic display data, said bloodstream data and said control signals as an address, outputs said combined imaging data for display.

10. An ultrasonic diagnostic system according to claim 9, wherein each of said memories stores a plurality of data groups each of which are converted into imaging data based upon different gamma; wherein the data converted into imaging data is selected according to said control signals in said address.

11. An ultrasonic diagnostic system according to claim 10, wherein said plurality of includes memories comprises first RAMs for respective R-signal, G-signal and B-signal outputs, each of which first RAMs combines said data from said two bloodstream flow data storages as imaging data; and second RAMs for respective R-signal, G-signal and B-signal outputs, each of which second RAMs combines the imaging data from corresponding of said first RAMs with said tomographic data as the combined imaging data output for display by said display means.

12. An ultrasonic diagnostic system according to claim 11, wherein said memory means further comprises a graphic memory for storing graphic display data and a character memory for storing alphanumeric display data.

13. An ultrasonic diagnostic system according to claim 12, wherein said bloodstream data selection means outputs said tomographic display data, said graphic data, said alphanumeric data, and said data from said two bloodstream flow data storages.

14. An ultrasonic diagnostic system according to claim 13, wherein said combining and color-signal encoding means comprises:

an imaging data color palette storing data for combining and color-encoding said tomographic data and bloodstream data;

a graphic data color palette storing data for color-encoding said graphic data; and a character data color palette storing data for color-encoding said character data.

15. An ultrasonic diagnostic system according to claim 14, wherein said combining and color-signal encoding means further comprises a switch which selects one of said color palettes for output of said display data.

16. An ultrasonic diagnostic system according to claim 5, wherein said external storage comprises an analog recorder for recording video combined signals, and wherein said recording means comprises an encoder which produces a pseudo-video combined signal by analyzing said tomographic display data and said data from said two bloodstream flow data storages as equivalent to R, G, and B video signals.

17. An ultrasonic diagnostic system according to claim 16, further comprising a decoder which decodes a video combined signal regenerated from said analog recorder to obtain said tomographic display data together with said data from the two of said bloodstream flow data storages, as selected by said bloodstream data selection means.

18. An ultrasonic diagnostic system according to claim 17, wherein said analog recorder comprises a video tape recorder.

19. An ultrasonic diagnostic system according to claim 5, wherein said external storage comprising a digital recorder, and wherein said recording means comprises a buffer memory for temporarily storing the data read out by said bloodstream data selection means for recording into said digital recorder, and for temporarily storing data retrieved from said digital recorder for input to said selection means.

20. An ultrasonic diagnostic system according to claim 19, wherein said digital recorder comprises a magnetic-optical disc device.

* * * * *